United States Patent
Grabosch

(10) Patent No.: US 9,808,796 B2
(45) Date of Patent: Nov. 7, 2017

(54) PIPETTE AND METHOD FOR PIPETTING

(71) Applicant: Sartorius Lab Instruments GmbH & Co. KG, Goettingen (DE)

(72) Inventor: Matthias Grabosch, Bovenden (DE)

(73) Assignee: Sartorius Lab Instruments GmbH & Co. KG, Goettingen (DE)

( * ) Notice: Subject to any disclaimer, the term of this patent is extended or adjusted under 35 U.S.C. 154(b) by 187 days.

(21) Appl. No.: 14/711,048

(22) Filed: May 13, 2015

(65) Prior Publication Data

US 2015/0238953 A1    Aug. 27, 2015

Related U.S. Application Data

(63) Continuation of application No. PCT/EP2013/003373, filed on Nov. 8, 2013.

(30) Foreign Application Priority Data

Nov. 13, 2012  (DE) .................. 10 2012 022 121

(51) Int. Cl.
*B01L 3/02* (2006.01)
*G01N 1/14* (2006.01)

(52) U.S. Cl.
CPC ............. *B01L 3/0217* (2013.01); *B01L 3/021* (2013.01); *B01L 3/0203* (2013.01);
(Continued)

(58) Field of Classification Search
CPC .... B01L 3/0217; B01L 3/0203; B01L 3/0206; B01L 3/0293; B01L 3/021; G01N 2001/1436; G01N 2001/1427
See application file for complete search history.

(56) References Cited

U.S. PATENT DOCUMENTS 3,693,640 A * 9/1972 Wettlen .................. A23C 7/02
                                                        134/169 R
4,118,152 A   10/1978 Bron
(Continued)

FOREIGN PATENT DOCUMENTS

DE   19632348 C1   11/1997
DE   29703080 U1    6/1998
(Continued)

OTHER PUBLICATIONS

International Search Report in counterpart International Application No. PCT/EP2013/003373, mailed Feb. 17, 2014.
(Continued)

*Primary Examiner* — Paul West
(74) *Attorney, Agent, or Firm* — Edell, Shapiro & Finnan, LLC

(57) ABSTRACT

A pipette has a first chamber and a second chamber that connects to the first chamber and extends with an outlet channel to a pipette tip. The chambers are separated from one another by a longitudinally displaceable piston having a piston non-return valve. The second chamber has a chamber non-return valve which is arranged upstream of the outlet channel. An associated method includes recirculating the liquid in the first chamber, filling the first chamber with the liquid via a direct feed line, filling the second chamber with the liquid from the first chamber by pulling back the piston in the filling position toward the first chamber with the piston non-return valve open and with the chamber non-return valve closed, and emptying the second chamber by advancing the piston in the emptying position towards the outlet channel, with the piston non-return valve closed and the chamber non-return valve open.

13 Claims, 2 Drawing Sheets

(52) U.S. Cl.
CPC .......... *B01L 3/0206* (2013.01); *B01L 3/0293* (2013.01); *B01L 2200/141* (2013.01); *G01N 2001/1427* (2013.01); *G01N 2001/1436* (2013.01)

(56) References Cited

U.S. PATENT DOCUMENTS

| | | | |
|---|---|---|---|
| 5,533,879 A | | 7/1996 | Chen |
| 5,826,613 A | * | 10/1998 | Schalk .................... F16K 1/123 137/219 |
| 6,220,835 B1 | | 4/2001 | Salmela et al. |
| 6,367,664 B1 | | 4/2002 | Bunyan et al. |

FOREIGN PATENT DOCUMENTS

| | | |
|---|---|---|
| DE | 19827035 A1 | 12/1998 |
| GB | 221032 A | 9/1924 |

OTHER PUBLICATIONS

English translation of International Preliminary Examination Report on Patentability in counterpart International Application No. PCT/EP2013/003373.

Office Action in corresponding German Application No. 102012022121.5, dated Jul. 19, 2013, along with an English translation.

Written Opinion in counterpart International Application No. PCT/EP2013/003373, mailed Feb. 17, 2014.

* cited by examiner

PIPETTE AND METHOD FOR PIPETTING

CROSS REFERENCE TO RELATED APPLICATIONS

This is a Continuation of International Application PCT/EP2013/003373, which has an international filing date of Nov. 8, 2013, and the disclosure of which is incorporated in its entirety into the present Continuation by reference. The following disclosure is also based on and claims the benefit of and priority under 35 U.S.C. §119(a) to German Patent Application No. DE 10 2012 022 121.5, filed Nov. 13, 2012, which is also incorporated in its entirety into the present Continuation by reference.

FIELD OF THE INVENTION

The invention relates to a pipette comprising a first chamber, which is arranged in a housing, and a second chamber, also arranged in the housing, which connects to said first chamber and extends with an outlet channel to a pipette tip, said chambers being separated from one another by a longitudinally displaceable piston having a piston non-return valve, and comprising a chamber non-return valve, which is arranged upstream of the outlet channel and is a part of the second chamber, wherein the first chamber can be filled with a liquid by way of a direct feed line.

Furthermore, the invention relates to a method for pipetting a liquid with the pipette.

BACKGROUND

When pipetting, a liquid that is be pipetted is usually drawn into a chamber of the pipette through the pipette tip, in order to subsequently dispense the liquid in a specifiable quantity through the pipette tip.

For example, DE 26 58 592 A1 discloses a pipette comprising a first chamber, which is arranged in a housing, and a second chamber, which connects to said first chamber and extends to a pipette tip. In this case the pipette tip has an outlet channel, by means of which the first chamber can also be filled with the liquid to be pipetted. At the same time the two chambers are separated from one another by a longitudinally displaceable piston, which has a non-return valve. A chamber non-return valve is disposed upstream of the outlet channel and extends to the second chamber. During aspiration of only one liquid, an auxiliary piston, which is guided in the chamber non-return valve, is removed so that the chamber non-return valve is bypassed.

One disadvantage of the pipettes known from the prior art is that in the course of filling the chambers, the aspiration of the liquid through of the pipette tip may cause contamination. An additional drawback is that during aspiration of the liquid, the gases from the surrounding area come into contact with the liquid, or the ambient air is also drawn in. In particular, when using ultrapure water as the liquid to be pipetted, contact with the atmosphere is disadvantageous, because carbon dioxide is dissolved into the ultrapure water and, in so doing, forms carbonic acid.

Furthermore, U.S. Pat. No. 6,220,835 B1 discloses a dispensing device comprising a first chamber and a second chamber, which connects to said first chamber and extends to an outlet channel, said chambers being separated from one another by a longitudinally displaceable piston having a piston non-return valve. The second chamber has a chamber non-return valve that is arranged upstream of the outlet channel. The first chamber can be filled with a liquid by means of a direct feed line.

The drawback with the known device is that when a liquid, which is to be pipetted, is filled into an intermediate tank, in particular, when ultrapure water is the liquid to be pipetted, the situation may arise that inorganic ions or constituents dissolve out. As a result, the quality of the liquid medium may decline.

GB 221 032 A discloses a syringe or sprayer, which comprises a first and a second chamber in a cylindrical housing, where both chambers are separated from one another by a longitudinally displaceable piston having a non-return valve. A non-return valve is disposed upstream of the second chamber, which is connected to the outlet channel, and extends to the outlet channel. The first chamber can be filled with a liquid by means of a feed line. At the same time the liquid from the first chamber can be drained only through the second chamber and the syringe outlet. On the end facing away from the syringe outlet, the housing has a mount, to which a spare nozzle can be screwed. The spare nozzle is apparently provided for the purpose of replacing the nozzle. The drawback with this known syringe or sprayer is that if a person skilled in this art were to use said syringe or sprayer to fill a liquid, which is to be pipetted, into an intermediate tank, especially if ultrapure water were to be the liquid that is to be pipetted, then the situation might arise that inorganic ions or constituents would dissolve out. As a result, the quality of the liquid medium may decline in an undesired way.

Furthermore, the drawback with the known device is that the piston consists of a first head portion, which does not seal on the periphery and is connected to a piston rod, and a sealing member, which seals and is arranged in such a way that it can be moved longitudinally relative to the head portion. Furthermore, said piston has a through-channel, which is closed by a stop face of the head portion, when the head portion is moved in the direction of the outlet channel.

DE 198 27 035 A1 discloses a dispensing device comprising a first chamber and a second chamber, which connects to said first chamber and extends to a delivery valve, said chambers being separated from one another by a longitudinally displaceable piston having a piston non-return valve. The first chamber can be filled, in particular, with a viscous liquid by means of a direct feed line. This device also has the drawbacks described above.

U.S. Pat. No. 4,118,152 A discloses a dosing pump, which draws a liquid into a first chamber by means of a piston over a suction line and a suction valve and then feeds the liquid through a piston valve into a second chamber and, upon filling the first chamber from the second chamber, discharges the liquid through an outlet. The suction valve and the piston valve have opposing flow directions.

This dosing pump also has the drawbacks described above.

DE 196 32 348 C1 discloses a piston burette, which has a dosing chamber with two valves that are arranged next to each other, a suction valve and a discharge valve. A piston is used to draw in a liquid from a storage tank by way of the suction valve, where in this case the discharge valve is closed, and with the suction valve closed, the liquid is discharged from the dosing chamber by way of the discharge valve that is open.

This dosing pump also exhibits the drawbacks described above.

DE 297 03 080 U1 discloses a device for delivering liquids, which has a non-return valve. The non-return valve is arranged upstream of a discharge tube and consists of a valve ball, which is pressed against a valve seat by a valve spring.

SUMMARY

An object of the present invention is to improve the known pipettes in such a way that, when the chambers are being filled, no contamination and no contact with the atmosphere will take place, and to propose a method for pipetting a liquid. In particular, in combination with ultrapure water as the liquid to be pipetted, the object is to prevent inorganic ions or constituents from dissolving out.

The object with respect to the pipette is achieved in conjunction with the preamble of claim 1 in that the first chamber is connected by way of the feed line and an outlet line to a recirculation circuit of a storage tank containing a liquid that is to be pipetted or to an ultrapure water system.

Aspiration of the liquid to be pipetted through the pipette tip is reliably avoided by filling the first chamber by means of a direct or separate feed line and the chamber non-return valve. As a result, the drawbacks associated with the aspiration of the liquid through the pipette tip, such as contamination and undesired atmospheric contact, cease to apply.

The recirculation ensures that the high quality of the liquid medium stays at a constant high level. Due to the direct connection to the storage tank/an ultrapure water system, there is no need to fill the liquid to be pipetted/the ultrapure water to be pipetted into an intermediate tank, in which it is possible for inorganic ions or organic constituents to dissolve out. In addition, there are also the aforementioned advantages.

According to an additional preferred embodiment of the invention, the first and the second chambers form a common chamber. In this case the longitudinally displaceable piston divides the common chamber into the first and second chambers so that the piston determines by its position the volumes of the chambers. If the piston is moved in the direction of the pipette tip or the chamber non-return valve, then the volume of the first chamber decreases, while the volume of the second chamber increases accordingly.

According to another preferred embodiment of the invention, in a rest position the piston strikes against the chamber non-return valve, so that the second chamber exhibits its minimum volume, for example zero, whereas the first chamber exhibits its maximum volume. In the rest position the piston non-return valve and the chamber non-return valve are closed.

According to an additional preferred embodiment of the invention, in a filling position for filling the second chamber, the piston can be displaced in the direction of the first chamber. In the filling position the piston non-return valve is open, whereas the chamber non-return valve is closed.

According to another preferred embodiment of the invention, in an emptying position for emptying the second chamber by way of the outlet channel of the pipette tip, the piston can be displaced in the direction of the second chamber. By displacing the piston in the direction of the second chamber, the liquid to be pipetted can be discharged in a specified volume over the outlet channel of the pipette tip. In the emptying position the piston non-return valve is closed, whereas the chamber non-return valve is opened.

According to an additional preferred embodiment of the invention, the piston can be displaced by means of a drive that is disposed externally on the housing. In particular, the piston is connected to the drive by means of a piston rod. The drive can be designed, for example, as an electric motor.

According to another preferred embodiment of the invention, the parts that come into contact with the liquid are made of materials, such as polyvinylidene fluoride (PVDF), which release relatively few non-extractable constituents. This feature is advantageous, especially when using ultrapure water as the liquid that is to be pipetted.

The object with respect to the method is achieved in conjunction with the preamble of claim 12 in that the following steps are carried out:
a) filling the first chamber with a liquid using a direct feed line,
b) filling the second chamber with the liquid from the first chamber by pulling back the piston in the filling position in the direction of the first chamber with the piston non-return valve open and the chamber non-return valve closed, and
c) emptying the second chamber by pushing forward the piston in the emptying position in the direction of the outlet channel, which faces away from the first chamber, with the piston non-return valve closed and the chamber non-return valve open.

Aspiration of the liquid to be pipetted through the pipette tip is reliably prevented by filling the first chamber by way of a direct or separate feed line and the chamber non-return valve. As a result, the drawbacks associated with the aspiration of a liquid through the pipette tip, such as contamination and undesired atmospheric contact, cease to apply. The different levels of pressure resulting from the retraction and extension of the piston respectively open and close the non-return valves in the intended manner.

Additional features and advantages of the invention will be apparent from the following specific description and the drawings.

BRIEF DESCRIPTION OF THE DRAWINGS

The drawings show in.

DETAILED DESCRIPTION

Figures 1, 2:
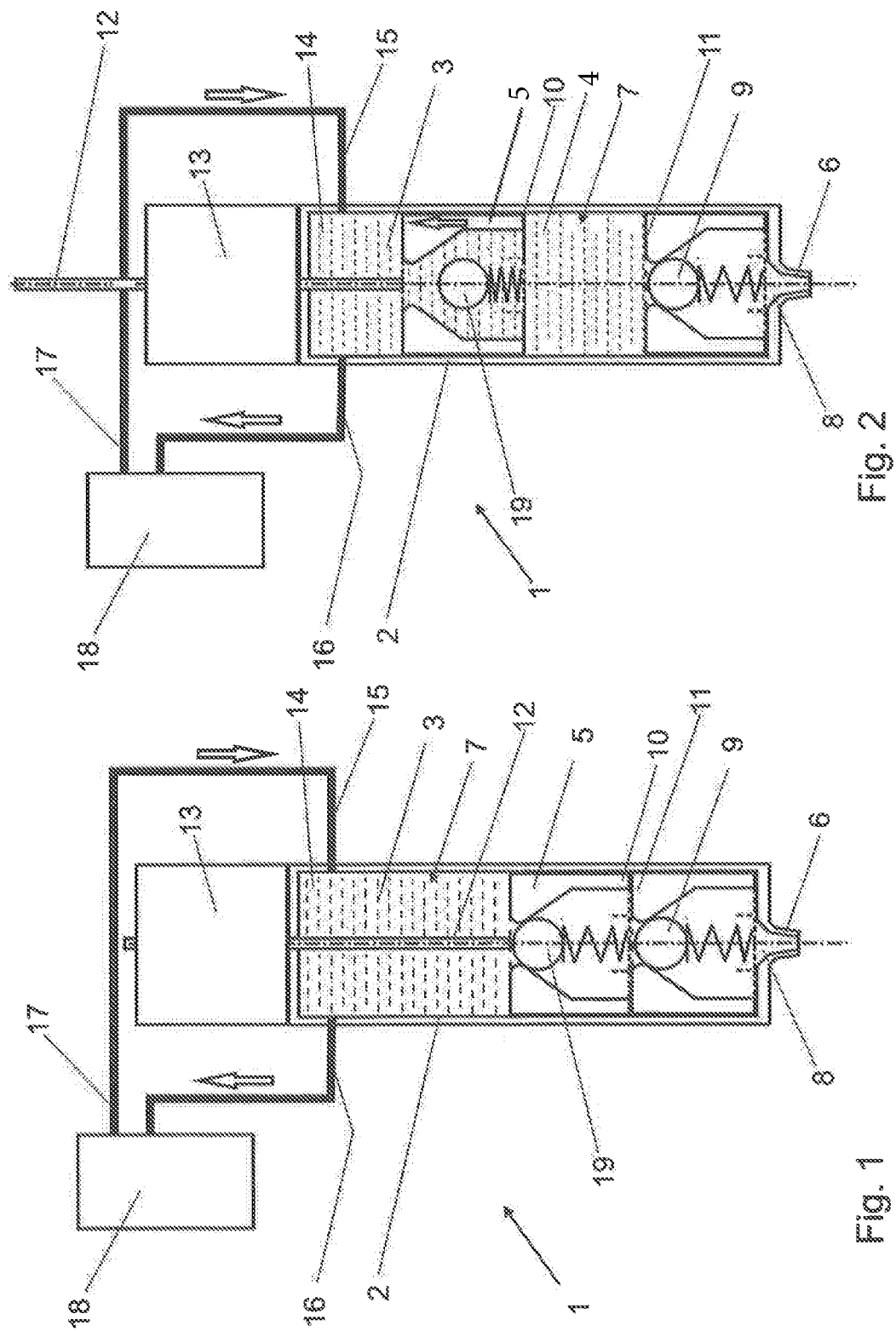
FIG. 1: a side elevation in the section of a pipette comprising a piston that is located in a rest position.
FIG. 2: a side elevation in the section of the pipette from FIG. 1, where in this case the piston is located in a filling position.

A pipette 1 consists in essence of a housing 2, a first chamber 3, a second chamber 4, a piston 5 and a pipette tip 6.

The first chamber 3 and the second chamber 4 form a common chamber 7, which is divided by the piston 5 into the first chamber 3 and the second chamber 4. As a result, the first chamber 3 and the second chamber 4 are separated from one another by the piston 5. The pipette tip 6 has an outlet channel 8, upstream of which a chamber non-return valve 9 is arranged in the direction of the second chamber 4. The chamber non-return valve 9 forms a stop with its chamber-sided end 11 relative to the pipette tip-sided end 10 of the piston 5. The piston 5 is mounted in a longitudinally displaceable manner in the common chamber 7 and is connected to a drive 13 via a piston rod 12.

The first chamber 3 is connected at its upper end 14, which faces away from the pipette tip 6, through a feed line 15 and an outlet line 16 to a recirculation circuit 17 of an ultrapure water system 18, such as, for example, the system offered by Sartorius under the name ARIUM®.

The piston 5 has a piston non-return valve 19, which enables a liquid to be filled from the first chamber 3 into the second chamber 4. Penetration of the liquid from the second chamber 4 into the first chamber 3 is prevented by the piston non-return valve 19. The chamber non-return valve 9, in turn, prevents a fluid, coming from outside, from penetrating through the outlet channel 8 into the second chamber 4.

According to FIG. 1, in a rest position the piston 5 strikes with its pipette tip-sided end 10 against the chamber-sided end 11 of the chamber non-return valve 9. As a result, the second chamber 4 has a minimum volume of zero, while the first chamber 3 exhibits its maximum volume. In the rest position the piston non-return valve 19 and the chamber non-return valve 9 are closed.

According to FIG. 2, in a filling position for filling the second chamber 4, the piston 5 is displaced in the direction of the first chamber 3. As a result, the piston non-return valve 19 of the piston 5 is opened, whereas the chamber non-return valve 9 remains in its closed position.

Figure 3:
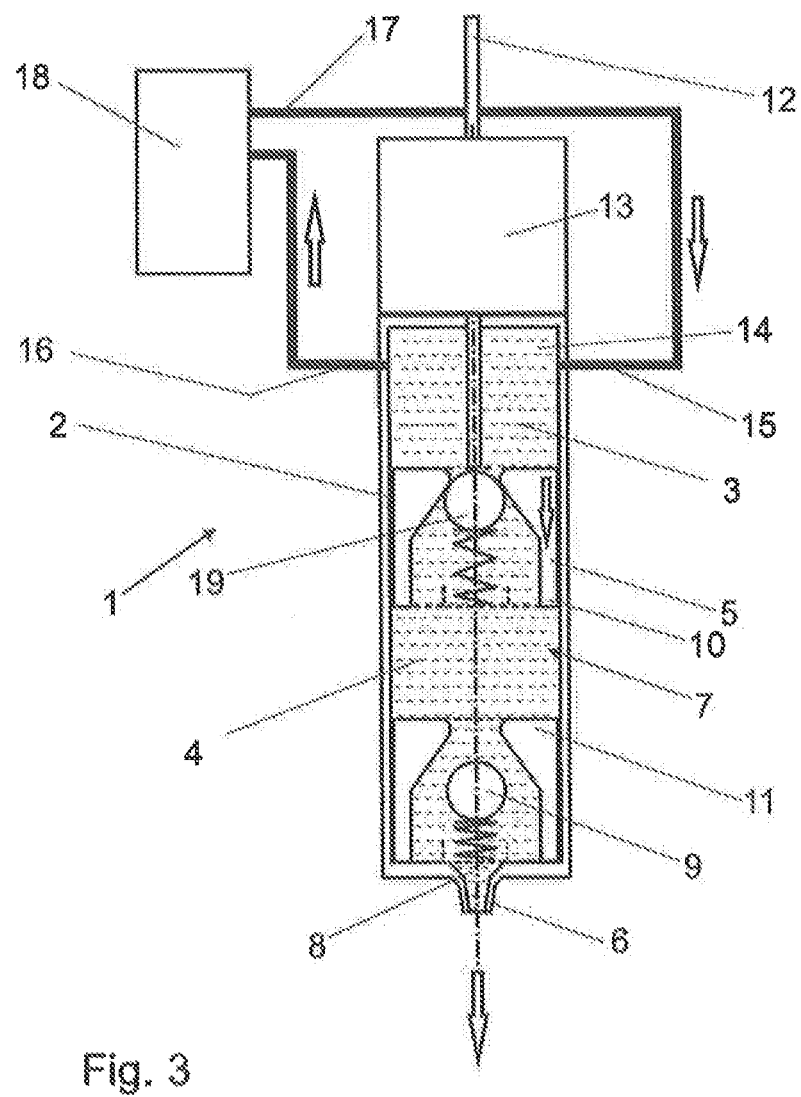
FIG. 3: a side elevation in the section of the pipette from FIG. 1, where in this case the piston is located in an emptying position for discharging a liquid from the pipette tip.

According to FIG. 3, in an emptying position or discharge position for emptying the second chamber 4 through the outlet channel 8, associated with the pipette tip 6, the piston 5 is displaced in the direction of the second chamber 4, i.e. in the direction of the pipette tip 6. As a result, the piston non-return valve 19 is closed, whereas the chamber non-return valve 9 is open, so that the liquid, which is located in the second chamber 4, is discharged through the outlet channel 8 of the pipette tip 6.

The parts that are shown in FIGS. 1 to 3 and that come into contact with the liquid are made of a polyvinylidene fluoride.

The embodiments that have been discussed in the detailed description and shown in the figures constitute embodiments of the present invention that are shown solely for illustrative purposes. The present disclosure enables those skilled in this art with a wide range of possible variations, all of which are intended to fall within the scope of the present invention.

LIST OF REFERENCE NUMERALS

1 pipette
2 housing
3 first chamber
4 second chamber
5 piston
6 pipette tip
7 common chamber
8 outlet channel of 6
9 chamber non-return valve
10 pipette tip-sided end of 9
11 chamber-sided end of 9
12 piston rod
13 drive
14 upper end of 3
15 feed line
16 outlet line
17 recirculation circuit
18 storage tank or ultrapure water system
19 piston non-return valve

What is claimed is:

1. A pipette comprising:
   a first chamber, arranged in a housing, and
   a second chamber, also arranged in the housing, which connects to the first chamber and extends through an outlet channel to a pipette tip,
   wherein the first and second chambers are separated from one another by a longitudinally displaceable piston having a piston non-return valve,
   wherein the second chamber comprises a chamber non-return valve, which is arranged upstream of the outlet channel,
   wherein the first chamber is configured to be filled with liquid via a direct feed line,
   wherein the first chamber is connected via the feed line and an outlet line to a storage tank for the liquid, and
   wherein the feed line, the outlet line, and the storage tank form a recirculation circuit for the liquid.

2. The pipette, as claimed in claim 1, wherein the first and the second chambers form a common chamber,
   the longitudinally displaceable piston divides the common chamber into the first and second chambers, and
   a position of the piston determines respective volumes of the first and second chambers.

3. The pipette, as claimed in claim 1, wherein in a rest position, the piston strikes towards the chamber non-return valve, such that the second chamber exhibits its minimum volume, whereas the first chamber exhibits its maximum volume.

4. The pipette, as claimed in claim 3, wherein in the rest position, the piston non-return valve and the chamber non-return valve are closed.

5. The pipette, as claimed in claim 1, wherein in a filling position for filling the second chamber, the piston is displaced towards the first chamber.

6. The pipette, as claimed in claim 5, wherein in the filling position, the piston non-return valve is open, and the chamber non-return valve is closed.

7. The pipette, as claimed in claim 1, wherein in an emptying position for emptying the second chamber by way of the outlet channel of the pipette tip, the piston is displaced towards the second chamber.

8. The pipette, as claimed in claim 7, wherein in the emptying position, the piston non-return valve is closed, and the chamber non-return valve is open.

9. The pipette, as claimed in claim 1, wherein the piston is displaced with a drive arranged externally to the housing.

10. The pipette, as claimed in claim 9, wherein the piston is connected to the drive via a piston rod.

11. The pipette, as claimed in claim 1, wherein parts of the pipette that come into contact with the liquid are made of polyvinylidene fluoride.

12. The pipette as claimed in claim 1, wherein the pipetting liquid is ultrapure water stored in a water system.

13. A method for pipetting a liquid with a pipette, the pipette comprising:
   a first chamber and a second chamber which connects to the first chamber and extends through an outlet channel to a pipette tip,
   wherein the first and second chambers are separated from one another by a longitudinally displaceable piston having a piston non-return valve,
   wherein the second chamber comprises a chamber non-return valve which is arranged upstream of the outlet channel,
   wherein the first chamber is configured to be filled with the liquid via a direct feed line,
   wherein the first chamber is connected via the feed line and an outlet line to a source for the liquid, and wherein the source, the feed line, the first chamber, and the outlet form a recirculation circuit for the liquid, said method comprising:

recirculating the liquid of the first chamber with the recirculation circuit, filling the first chamber with the liquid via the direct feed line, filling the second chamber with the liquid from the first chamber by pulling back the piston in the filling position towards the first chamber with the piston non-return valve open and the chamber non-return valve closed, and emptying the second chamber by advancing the piston in the emptying position toward the outlet channel, which faces away from the first chamber, with the piston non-return valve closed and the chamber non-return valve open.

\* \* \* \* \*